United States Patent [19]

Lidgren et al.

[11] Patent Number: 5,549,380
[45] Date of Patent: Aug. 27, 1996

[54] MIXING DEVICE FOR MANUFACTURING BONE CEMENT

[75] Inventors: Lars Å A. Lidgren, Lund, Sweden; Hans J. Bauer, Flomborn, Germany

[73] Assignee: MIT AB, Sjobo, Sweden

[21] Appl. No.: 397,987

[22] Filed: Mar. 3, 1995

[30] Foreign Application Priority Data

Mar. 21, 1994 [DE] Germany .................. 44 09 610.0

[51] Int. Cl.$^6$ ................................. B01F 13/06
[52] U.S. Cl. .................. 366/139; 366/189; 366/256; 206/222
[58] Field of Search .................. 366/129, 130, 366/139, 189, 255–260, 332–335; 206/219–222; 604/411, 414–416, 903; 606/86, 92–94

[56] References Cited

U.S. PATENT DOCUMENTS

| 3,739,947 | 6/1973 | Baumann et al. . | |
|---|---|---|---|
| 4,159,570 | 7/1979 | Baskas et al. . | |
| 4,193,698 | 3/1980 | Gartner | 206/219 X |
| 4,277,184 | 7/1981 | Solomon | 366/139 |
| 4,463,875 | 8/1984 | Tepic . | |
| 4,542,823 | 9/1985 | Frick | 206/220 |
| 4,676,655 | 6/1987 | Handler | 366/333 X |
| 4,721,390 | 1/1988 | Lidgren | 366/139 |
| 4,735,509 | 4/1988 | Rausch | 366/333 |
| 4,758,096 | 7/1988 | Gunnarsson | 366/139 |
| 4,772,031 | 9/1988 | Poppo | 206/219 X |
| 4,808,006 | 2/1989 | Kaufeler | 366/130 X |
| 4,858,759 | 8/1989 | Mauthe et al. | 206/221 |
| 4,902,728 | 2/1990 | Pietsch et al. | 523/115 |
| 4,973,168 | 11/1990 | Chan . | |
| 5,252,301 | 10/1993 | Nilson et al. | 366/255 X |
| 5,328,262 | 7/1994 | Lidgren et al. | 366/139 |
| 5,435,645 | 7/1995 | Faccioli et al. | 366/139 X |

FOREIGN PATENT DOCUMENTS

| 0194508 | 9/1986 | European Pat. Off. . | |
|---|---|---|---|
| 2447875 | 8/1980 | France . | |
| 1939316 | 2/1971 | Germany . | |
| 2800587 | 7/1979 | Germany | 206/219 |
| 2809646 | 9/1979 | Germany . | |
| 3221978 | 1/1983 | Germany . | |
| 4302230 | 8/1993 | Germany . | |
| 93220041 | 11/1993 | WIPO . | |

Primary Examiner—Charles E. Cooley
Attorney, Agent, or Firm—Tarolli, Sundheim, Covell, Tummino & Szabo

[57] ABSTRACT

A mixing device for mixing at least two substances, preferably a liquid monomer and a pulverulent polymer, for manufacturing bone cement. The two substances (16, 17) are mixed in a mixing space (9) in a mixing container (1), preferably in partial vacuum. The substances are provided separated from each other in a container (1, 18, respectively) for each substance. A mixing device (6) is provided in the mixing space (9) for mixing the two substances (16,17) therein. An opener (26), defined preferably by the mixing device (6), is provided for establishing at least one connection (27) between the separately provided substances (16, 17) and for bringing the substances in contact with each other for mixing. During opening of the connection (27) between the substances (16, 17) in the mixing space (9), the vacuum sucks one of the substances (16), preferably the liquid monomer, through the connection (27) to the other substance (17), preferably the pulverulent polymer.

9 Claims, 3 Drawing Sheets

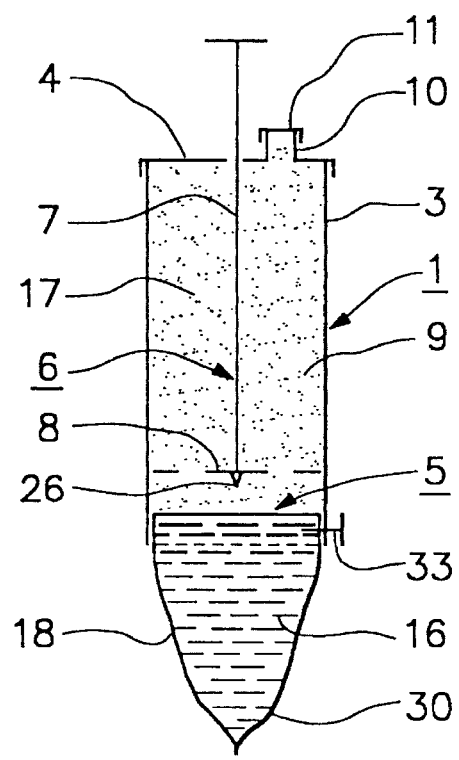
Fig.1
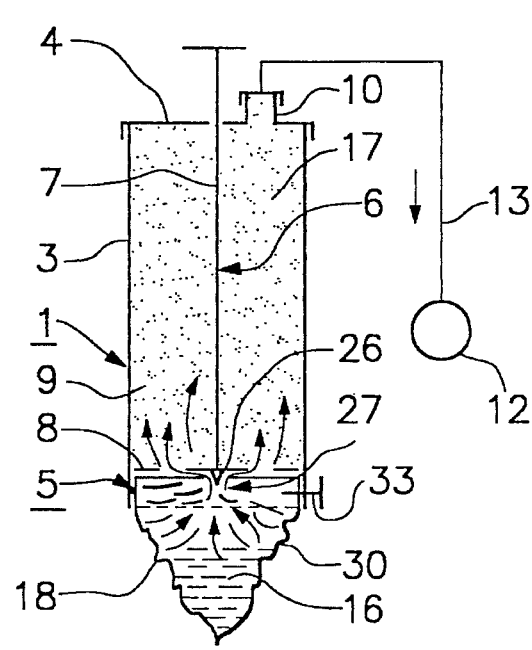
Fig.2
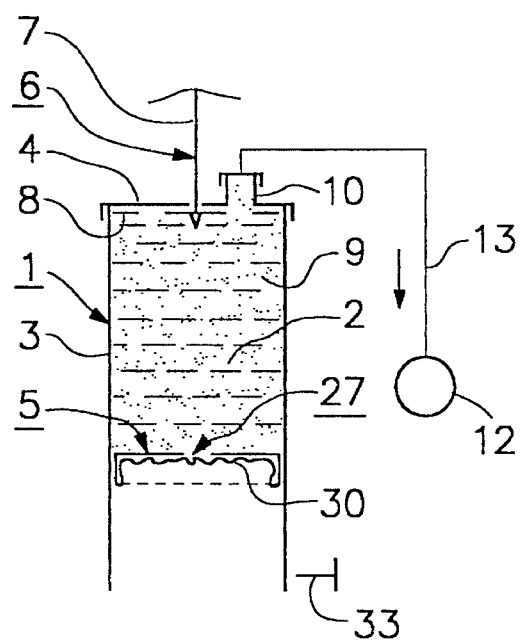
Fig.3
Fig.4

MIXING DEVICE FOR MANUFACTURING BONE CEMENT

BACKGROUND OF THE INVENTION

The present invention relates to a mixing device for mixing at least two substances, preferably a liquid monomer and a pulverulent polymer, for manufacturing bone cement, whereby the two substances are mixed in a mixing space in a mixing container, preferably in partial vacuum, and whereby the substances are provided separated from each other in one container for each substance.

In medicine, the implant technique has made substantial progress in recent years. Particularly the application methods for bone cement during implant of prostheses as well as the use of bone cement as place holder in the restorative surgery, have made astounding progress.

During the time of origin of bone cements, said bone cements were mixed in a cup or bowl at atmospheric pressure and temperature, kneaded by hand and formed into "sausages" and put into the defects to be filled and finally compressed by hand. These methods were for a long time the only possible application method for bone cement.

Then, an improvement in the form of an application through a cartridge was developed. Here too, the bone cement was mixed at normal atmospheric conditions, but then put in a cartridge and forced out through an orifice therein by means of a mechanical power transmission apparatus (pistol).

The next progress in the application method was the complete elimination of hand contact with the bone cement, whereby mixing was carried out in a special cup or bowl from which the mixed cement was transferred directly into the cartridge.

At these times, the term of life of implanted prostheses was mainly dependent on the skill of the surgeon. The term of life of the implants was dependent on the perfection with which the cement was mixed and applied. The term of life was not dependent on the quality of the prostheses (except for the commonly known shaft breakages), since the term of life for bone cement was far below that of the prostheses. Here, the physicians and scientists acknowledged an essential development deficit and stucked the principal reasons for the failure of the bone cements. In principal, two main reasons were found for the relatively short term of life of the bone cements. First, there was an incomplete mixing of the monomers with the polymers, which lead to low and various primary strengths within the cement casing or mantle around the prostheses and which because of uncombined and polymerized monomer and polymer components lead to toxic problems and inflammatory tissue reactions. Secondly, examinations indicated mechanical inhomogenities in the cement caused by enclosed air bubbles which have a substantial negative influence on the fatigue strength of the bone cement. However, coarse defects because of enclosed air bubbles also caused a premature breakage of the cement casing or mantle.

After a substantial reduction or elimination of infections by the integration of antibacterial active substances in the bone cements, which also prolonged the term of life of cemented prostheses, it was clearly necessary also to improve the mechanical properties of the bone cements in order to thereby further increase the term of life of the prostheses.

Acknowledging these circumstances, L. Lidgren developed a method for mixing bone cements and at the same time reducing the pores therein. In accordance with this method, the bone cements were mixed under vacuum in the application cartridge. Thereby, the monomer was put into the cartridge, the polymer powder filled therein and the cartridge sealed with a mixing device. After generating a vacuum, the polymer was mixed with the monomer under vacuum. The components were allowed to complete their reaction, also under vacuum, and first thereafter the bone cement was discharged from the cartridge through a snorkel or discharge pipe by means of a pistol. This system for mixing and applying bone cement is commercially available under the name "Optivac" from the company MIT AB and corresponding studies have proven its efficiency and reliability.

Experiments have shown that thanks to such a mixing procedure it is possible to substantially reduce the porosity (number and size of the air bubbles) of the cement matrix and, thus, the mechanical strength of a cement mixed accordingly.

A literature survey regarding the abovementioned mixing of bone cements under vacuum follows after this description.

From the patent literature, U.S. Pat. Nos. 4,463,875 and 4,973,168 as well as EP patent application No. 0 194 508 should be mentioned.

U.S. Pat. No. 4,463,875 defines a mixing device, whereby two substances to be mixed are packed up beforehand in the mixing device separated from each other. The substances are brought in contact with each other and thereafter mixed. In order to do this, the package is loaded from the outside with reciprocating movements, so that the package is deformed and the substances thereby mixed. A drawback is here that with these mixing movements, no bone cement with the required quality can be obtained. Furthermore, a complex container design is required for carrying out these mixing movements.

In U.S. Pat. No. 4,973,168 there is described a mixing device, wherein one of the substances to be mixed is packed up in the mixing device beforehand, while the other substance is packed up in a separate container independent of the mixing device. For mixing the substances, the container is emptied into the mixing device, whereafter the substance from the container is mixed with the substance already present in the mixing device by means of an inner mixing means. A drawback herewith is that a separate container is required for one of the substances and that there is a risk for that the separate container is not completely emptied or that a part of the substance in the separate container is spilled out and, thereby, the bone cement produces does not fulfill the quality demands set.

EP patent application No. 0 194 508 describes a mixing device for mixing other substances, whereby no vacuum is generated.

The object of the present invention is to provide a mixing device which renders it possible to improve the present mixing technique and to exclude errors in the preparation before mixing.

This is arrived at according to the invention by means of the characterizing features of the claims.

By means of these features it is particularly provided for that no transfer of substances is required and spill out of at least one substance is avoided, and that the substances also are sufficiently mixed for obtaining a bone cement with the required quality.

Hereby, without additional manipulations, the cement components can be located sterile ready for mixing in the mixing container, which, inter alia, leads to a reduction of the technical manipulations and minimization of the environmental danger and the amounts of waste. Furthermore, the contamination risk through the bone cement is reduced and no additional amounts of waste are produced. Errors in the order of actions taken during mixing are eliminated.

BRIEF DESCRIPTION OF THE DRAWINGS

The mixing device according to the invention will be further described below with reference to the accompanying drawings, in which:

FIG. 1 with a side view schematically illustrates a mixing container according to the invention, whereby two substances are provided separated from each other in two containers;

FIG. 2 schematically illustrates the mixing container of FIG. 1 during opening of a connection between the two containers, whereby a vacuum is generated in one of the containers;

FIG. 3 schematically illustrates the mixing container of FIG. 1 during mixing of the substances in a mixing space wherein vacuum reigns;

FIG. 4 schematically illustrates the mixing container of FIG. 1 during collection under vacuum in the mixing space of the bone cement made upn of the substances;

DESCRIPTION OF PREFERRED EMBODIMENT

Figure 5:
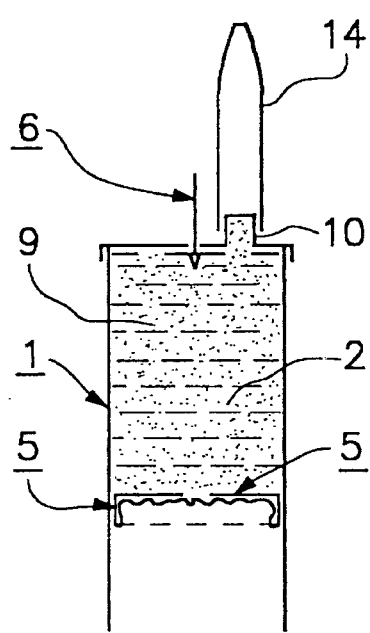
FIG. 5 schematically illustrates the mixing container of FIG. 1 with a discharge pipe connected thereto FIG. 6 schematically illustrates the mixing container of FIG. 1 during discharge of the bone cement by means of a pressure device.

The mixing container 1 illustrated in FIG. 1 has the form of a cartridge in which bone cement 2 is prepared and by means of which said bone cement is applied. This mixing container 1 preferably consists of a cylindrical container 3 which is sealed on the side by means of a cap 4 and on the opposite side by means of a displaceable piston 5. A mixing means 6 consists of a handle 7 and an agitating means 8 which is attached to said handle and located in a mixing space 9. The handle 7 is elongated in shape and displaceable and preferably also rotatably mounted or lodged in the cap 4, so that it can be displaced and rotated from the outside for reciprocal movement and preferably rotation of the agitating means 8 in the mixing space 9 and thus, mixing of the substances in said mixing space.

The cap 4 is provided with a connection pipe 10 which is sealable by means of a removable closure 11. A vacuum generating device 12 can through a hose 13 be connected with the connection pipe 10 (see FIG. 2) for generating a partial vacuum, preferably a vacuum of 60–95%, in the mixing space 9. Furthermore, a discharge pipe 14 can be attached to the connection pipe 10 (see FIGS. 5 and 6) for discharge therethrough of ready-made bone cement 2 from the mixing space 9 for application of said bone cement. Hereby, the bone cement 2 is pressed out of the mixing space 9 by means of the piston 5, whereby the piston is displaced by means of a pressure device 15, e.g. a pressure pistol or pressure gun (see FIG. 6).

One of the substances 17, preferably pulverulent polymer, is provided in the mixing space 9 and another substance 16, preferably liquid monomer, is provided in a container 18 separated from said mixing space. These substances 16, 17 are brought in contact with each other and mixed for producing bone cement 2 therefrom.

The piston 5 consists of a wall 19 and a sleeve-like member 20 which extends from the wall 19 in outwards direction relative to the mixing space 9. The outer side 21 of the wall 19 and the member 20 sealingly and displaceably engage the inner side 22 of the cylindrical container 3. A connection aperture 24 which is provided in the centre of the wall is sealed by means of a diaphragm 25. This diaphragm is opened by means of an opener 26, e.g. penetrated with a mandrel 26 on the agitating means 8, so that the wall 19 is opened and thus a connection 27 between the interior of the container 18 and the mixing space 9 as well. The sleeve-like member 20 may be cylindrical in shape and is on the outer side 21 provided with a groove 28 which extends circumferentially around said member 20. A sleeve-like end portion 29 of the container 18 is engaged in the groove 28, surrounds the sleeve-like member 20 of the piston 5 and is sealingly provided thereon.

The walls 30 of the container 18 consist of e.g. several layers, whereby an inner layer 31 is made of plastic, e.g. polyethylene, and an outer layer 32 of metallic material, e.g. aluminum.

The inner layer 31 engages the sleeve-like member 20 of the piston 5, which member 20 preferably consists of the same or a similar plastic material, e.g. polyethylene, as said inner layer 31. The plastic material of the piston 5 and of the inner layer 31 of the container 18 can be confounded with each other by means of a heat treatment, whereby the heat is provided by means of e.g. ultra welding.

In order to carry out the mixing operation, the mixing space 9 of the mixing container 1 is preferably at the spot, e.g. in an operating theatre wherein the mixing is to be carried through, connected with the vacuum generating device 12, whereby a partial vacuum is generated in said mixing space. Thereafter the mixing means 6 is used as opener 26, whereby the mandrel 26 is pushed through the diaphragm 25. Thanks to the connection 27 thus provided, the partial vacuum immediately affects the monomer 16 in the container 18 and results in that said monomer is sucked out of the container 18 and into the mixing space 9, i.e. flows to the polymer 17 therein (see FIG. 2). The walls 30 of the container 18 are designed (e.g. flexible and/or elastic) so that said walls thereby are drawn together, whereby the container 18 is completely or almost completely emptied (see FIG. 3).

When the monomer 16 is brought in contact with the polymer 17 in the mixing space 9, mixing occurs in that the mixing means 6 used for mixing is moved reciprocally in the mixing space 9 and eventually rotated until the monomer 16 and polymer 17 are sufficiently mixed (see FIG. 3). During this mixing, partial vacuum is preferably generated in the mixing space 9 by means of the vacuum generating device 12. Thereafter, a retaining means 33 which retains the piston 5 at an end portion of the cylindrical container 3, is removed (see FIG. 4), whereby the partial vacuum in the mixing space 9 sucks the piston 5 into the container 3. Hereby, the bone cement 2 and adhering lumps of bone cement at different spots in the mixing space 9 are collected in the mixing space at the cap 4.

Figure 6:
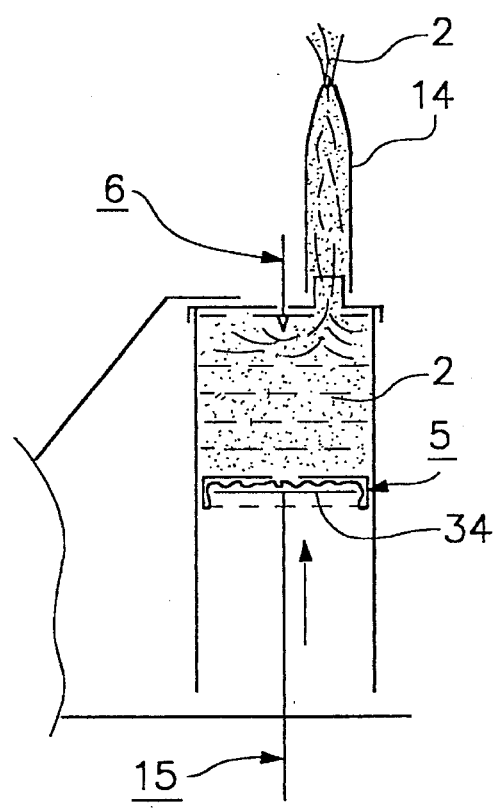
Figure 7:
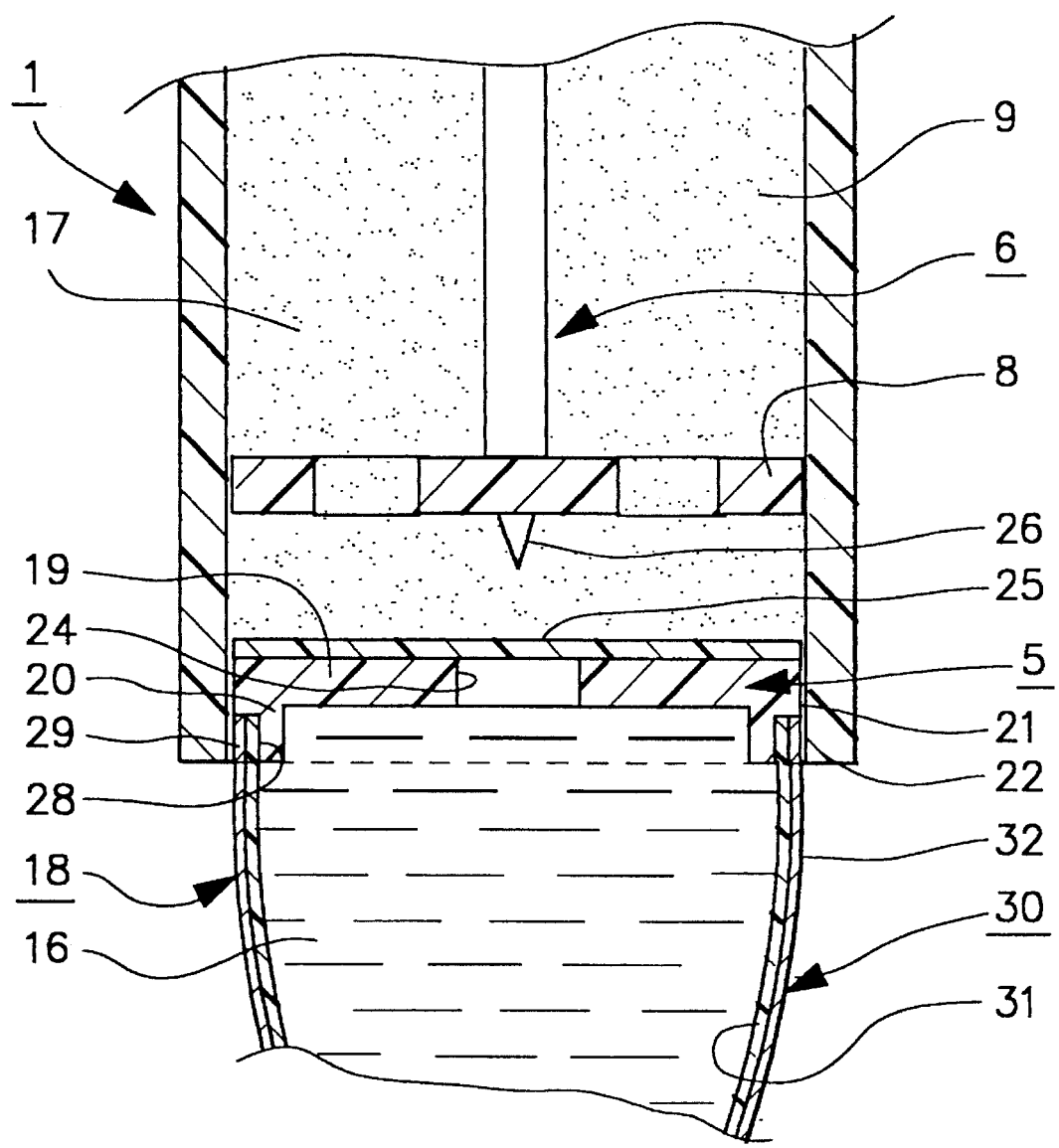
FIG. 7 is an enlarged section through a part of the mixing container of FIG. 1.

For emptying the mixing space 9, the hose 13 to the vacuum generating device 12 is removed from the connection pipe 10 and the discharge pipe 14 connected therewith (see FIG. 5). Thereafter, the mixing container 1 is placed in the pressure device 15 and the piston 5 by means of said pressure device pressed or moved towards the cap 4, whereby the bone cement 2 is pressed out of the mixing space 9 and discharged through the discharge pipe 14. The piston 5 is displaced with a pressure means 34 of the pressure device 15, whereby the container walls 30 are situated between the piston 5 and the pressure means 34. The container walls 30 may preferably take place in the sleeve-like member 20 of the piston 5 and/or be sucked thereinto and does not thereby prevent the pressure means 34 from being pushed into said sleeve-like member 20 (see FIG. 6).

The walls 30 of the container 18 can be made of such metallic material that the substance 16 therein is protected from the radiation effect occurring during sterilization by means of radiation.

The container 18 as well as the interior of the mixing container 1 can be sterilized.

The embodiments described above and shown in the drawings may vary within the scope of the claims. Thus, the mixing container 1 may e.g. be a mixing cup or mixing bowl, from which the bone cement made therein is transferred to a cartridge for application therewith. Partial vacuum can lie within but also outside the range 60–95% and eventually be generated beforehand in the mixing container 1.

The substance 17 can be packed up in an additional container located in the mixing space 9; the piston 5 and/or the container 18 may have another shape/shapes; the container 18, however, can be located in another position than at the piston 5. The opener for opening the wall 19 is described as a mandrel 26 on the mixing means 6, but may consist of another means provided in another way.

Having described the invention, the following is claimed:

1. A mixing device for mixing a first substance and a second substance for manufacturing bone cement comprising: a mixing container defining a mixing space, said first substance being contained in said mixing space, said mixing container comprising a piston movable in said mixing space to displace substance from said mixing space;

means for creating a vacuum in said mixing space;

a second container, said second substance being contained in said second container, said piston being a wall of said second container, said piston separating said second substance in said second container from said first substance in said mixing space;

a movable mixing means in said mixing space comprising an opener thereon;

means for moving said mixing means to (i) provide an opening in said piston, said opening allowing the vacuum in said mixing space to suck said second substance into said mixing space, and (ii) mix said first and second substances in said mixing space; and means for moving said piston to displace said mixed first and second substance from said mixing space.

2. A mixing device according to claim 1 wherein substantially all of said second substance in said second container is sucked into said mixing space by the vacuum in said mixing space.

3. A mixing device according to claim 1 wherein said piston comprises a sleeve like member and said second container comprises a sleeve-like end portion disposed on said sleeve-like member of said piston.

4. A mixing device according to claim 3 wherein said piston comprises an outer side, said sleeve-like member comprises a groove, and said mixing container comprises an inner side, said sleeve-like end portion of said second container surrounding said sleeve-like member and being disposed within said groove, such that said sleeve-like end portion sealingly engages said outer side of said piston, said outer side of said piston engaging said inner side of said mixing container.

5. A mixing device according to claim 4 wherein said second container comprises an inner layer and an outer layer, said inner layer engaging said piston, said inner layer and said piston both being made of a plastic material wherein said inner layer and said piston are connected with each other through heating, said outer layer being made of a metallic material.

6. A mixing device according to claim 1 wherein said piston and said second container are connected with each other through heating.

7. A mixing device according to claim 1 wherein said second container comprises walls, and the vacuum in said mixing space creates a vacuum in said second container after said opening is formed in said piston, said walls of said second container being substantially drawn together by the vacuum in said second container.

8. A mixing device according to claim 7 wherein said piston comprises a sleeve-like member, said walls of said second container consisting of flexible material such that said walls are substantially sucked into said sleeve-like member of said piston by the vacuum in said second container.

9. A mixing device according to claim 8 wherein said means for moving said piston comprises a pressure means, said walls of said second container, after displacement of said piston by said pressure means, being located between said piston and said pressure means.

* * * * *